United States Patent [19]

Nakamura

[11] Patent Number: 4,644,940

[45] Date of Patent: Feb. 24, 1987

[54] HALLUX VALGUS BRACE

[76] Inventor: Toshiro Nakamura, Ha 132, Omori-cho, Oda-shi, Shimane, Japan

[21] Appl. No.: 714,184

[22] Filed: Mar. 20, 1985

[51] Int. Cl.[4] .......................... A61F 5/30; A61F 5/01
[52] U.S. Cl. ................................... 128/81 R; 128/153
[58] Field of Search .................... 128/81 R, 153, 165, 128/169

[56] References Cited

U.S. PATENT DOCUMENTS

| 1,055,810 | 3/1913 | Scholl | 128/81 R |
| 1,073,185 | 9/1913 | Turner | 128/153 |
| 1,245,468 | 11/1917 | Koppe | 128/81 R |
| 1,471,041 | 10/1923 | Levitt | 128/153 |
| 1,665,030 | 4/1928 | Hartwig | 128/81 R |
| 1,746,865 | 2/1930 | Page | 128/81 R |
| 2,596,038 | 5/1952 | Mayer | 128/81 R |

FOREIGN PATENT DOCUMENTS

| 704642 | 3/1965 | Canada | 128/81 R |
| 126918 | 7/1928 | Switzerland | 128/81 R |
| 19607 | of 1903 | United Kingdom | 128/153 |

Primary Examiner—Edgar S. Burr
Assistant Examiner—Tonya Eckstine
Attorney, Agent, or Firm—Darby & Darby

[57] ABSTRACT

A hallux-valgus-remedy brace comprising a bag portion which embraces the hallux and two stretchable belts fixed to the bag portion, one of the belts being provided near the bag portion with an inserting portion which allows the other belt to pass through it.

1 Claim, 6 Drawing Figures

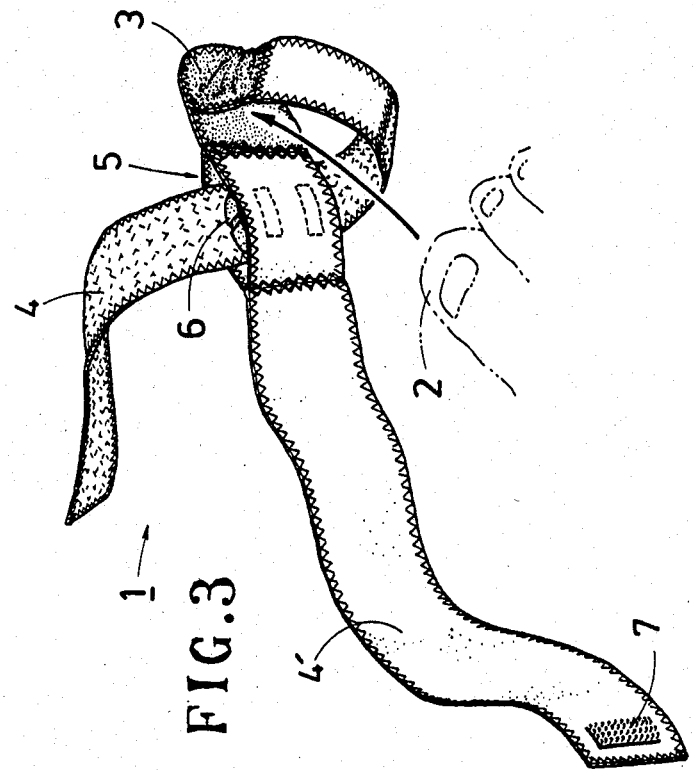
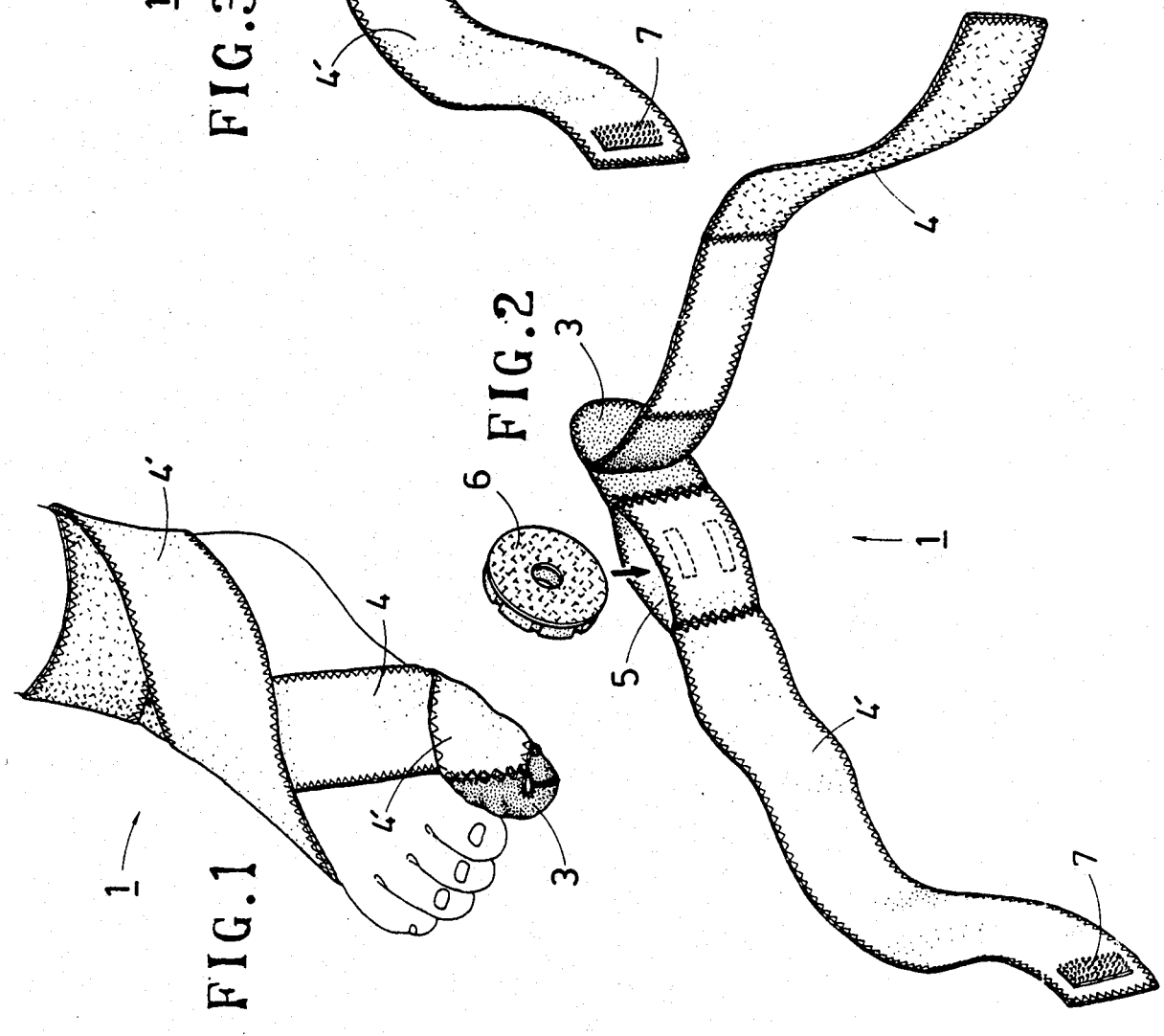

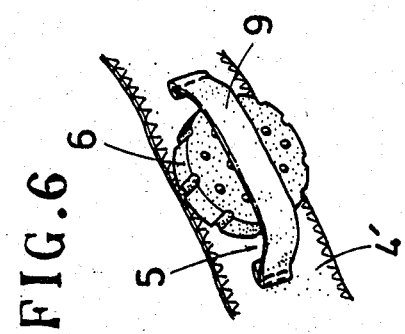
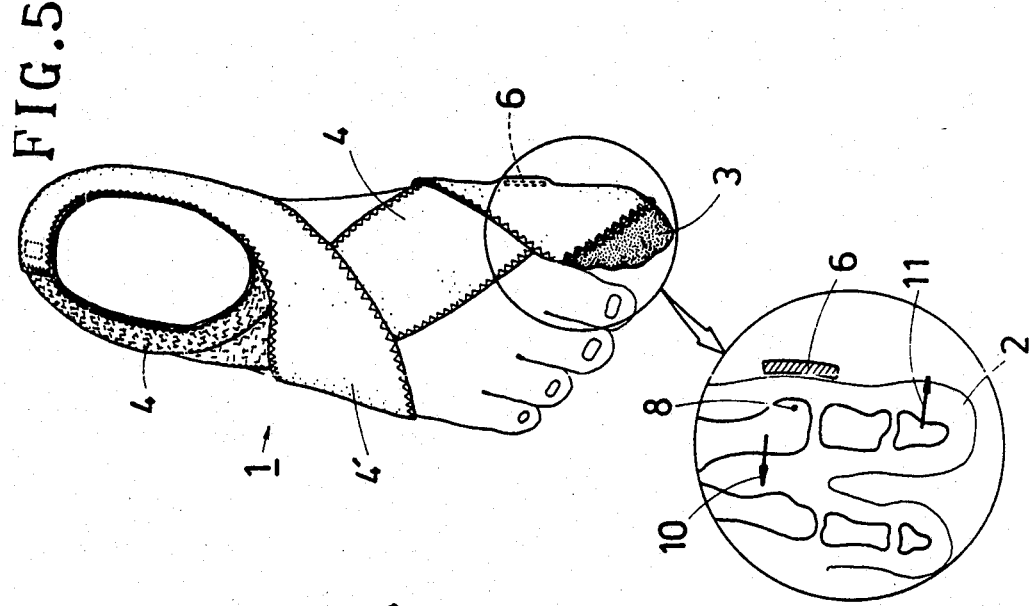
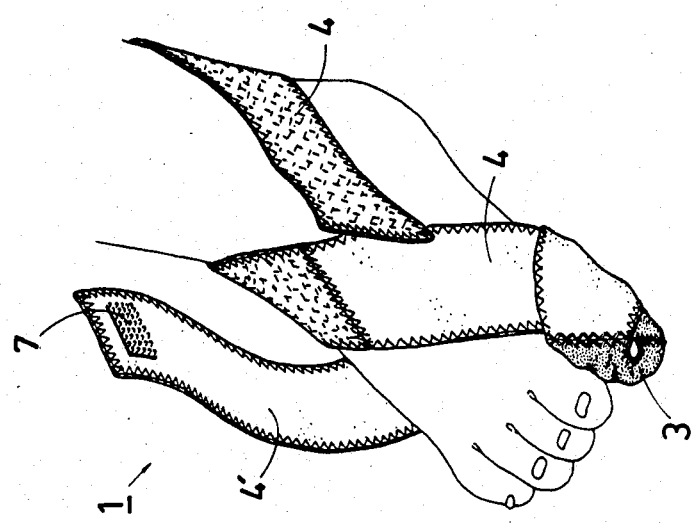

HALLUX VALGUS BRACE

BACKGROUND OF THE INVENTION

This invention relates to a brace used to conservatively correct the hallux from valgus.

"Hallux valgus" denotes a state or symptom of the hallux crooked toward the second toe. It had been attributed to the use of inadequate shoes (particularly shoes with pointed toes). At present, however, inadequate shoes are considered not the primary cause, although it may be a significant factor for worsening the deformation or the symptom. The primary causes are tumefaction of the head of first metatersal, abnormal first tarsometatarsal joint, abnormal muscular abductor pollicis or musculus adductor pollicis, abnormal joint between the first metatersal head and sesamoid, longer and larger first metatersal than second metatersal, and reluxed ligament. In any case, the first metatersal is excessively bent inward and then bent outward at the metatarsophalangeal joint, and the hallux is bent outward and intensely twisted relative to the other four toes, thus appearing in many cases to be opposite to them. When the deformation is noticeable, the inside of the first metatersal head grows larger and with a formation of bursa orcallus results in further enlarged projection. This bone projection and bursa together are commonly called a "bunion". Oppression and rubbing by shoes on this part can cause decubitus or bursitis and in some periosteomylitis circumscriptus.

In Europe and America wherein more cases are found than in Japan, a large variety of methods of operation have been disclosed (conventional methods of correcting a bunion include cutting off the head of first metatersal, a combination of osteotomy and tendotomy, new joint formation by implanting, etc.). The many different approaches to correcting the bunion shows that no single method is available that gives excellent results.

Surgical operation of a hallux valgus accompanied by congential arthrochalasis or nervimuscular disease is said to have a relapse rate of 50% or more. In such a case, operation should be avoided.

In addition, such a high degree of deformation as requiring osteotomy of the first metatersal is rare, and in Japan where the operation is not well developed, conservative treatment is almost always chosen as the method of treatment.

However, the conventional "brace remedy" has a number of drawbacks. The feet are an only region of the body that contact the ground when standing or walking. Thus, a brace should naturally not hinder such action. Two methods available for hallux valgus correction are pressing the hallux from the second-toe side or pulling it from the opposite side, but either of them is difficult to perform effectively in daily life such as wearing shoes or sandals, walking with it put on, and repeating putting it on and off. Thus, the patient prefers to avoid braces which are, for example, rigid, bulky, or troublesome to handle even if prescribed. As the last resort to make up such drawback, the manufacturers have provided two types of brace for selection by patients; a "waking brace" which cannot be expected to have sufficient effect and a "night brace" which is effective but not suitable to walking since it is rigid and bulky.

It has been a common practice to manufacture braces one by one according to the size and condition of individual patient particularly for braces made of metal. Consequently, the cost has been very high.

SUMMARY OF THE INVENTION

It is an object of the present invention to provide a brace having high remedial effect to hallux valgus.

Another object of the invention is to provide a brace for correcting a hallux valgus condition that is comfortable to wear.

A further object of the invention is to provide a brace for correcting a hallux valgus condition that is easy to handle and less expensive than conventional braces. A hallux-valgus-remedy brace according to the present invention comprises a bag portion which embraces at least part of the hallux, and two belts somewhat stretchable and united or sewed or bonded to the bag portion, one of the belts being provided near the bag portion with an inserting portion for passing the other belt therethrough.

BRIEF DESCRIPTION OF THE DRAWINGS

FIG. 1 is a perspective view showing application of an example of the hallux-valgus-remedy brace according to the invention.

FIG. 2 is a perspective illustration of the brace shown in FIG. 1.

FIGS. 3 and 4 are perspective views illustrating the method of applying the brace.

FIG. 5 is a schematic plan view showing the usage of the hallux-valgus-remedy brace according to the invention including a partially enlarged schematic view of the skeleton around the hallux.

FIG. 6 is a perspective view illustrating an embodiment of the inserting portion and others.

DETAILED DESCRIPTION OF THE INVENTION

FIG. 1 shows an embodiment of the invention actually applied on the right foot. The hallux-valgus-remedy brace 1 is mostly made of stretchable cloth. Hallux 2 is covered by a bag portion 3. The bag portion is in the middle of the brace 1 and fixed on its right and left side with stretchable belts 4, 4'. FIG. 2 is a perspective view of the hallux-valgus-remedy brace 1 in FIG. 1.

The belt 4 and belt 4' are different in type from each other, the belt 4' having an inserting portion 5 near the bag portion 3, and the belt 4 being passed through the inserting portion 5 when the brace is put on. In the inserting portion 5, a rather rigid sponge ring is bonded as a cushion member 6. To wear the hallux-valgus-remedy brace, the belt 4 is inserted through the inserting portion 5 (FIG. 3), and from the ring formed there, and the hallux 2 is put into the bag portion 3 so that the cushion member 6 comes in contact with the inside of the first metatersal head 8 (the projection beside the hallux root). The belt 5 is then wound around the instep to the ankle and the belt 4' from the sole round the instep to the ankle and both of the belts are secured with the face fastener 7 at the ankle.

As obvious from FIG. 2, the hallux-valgus-remedy brace 1 of the invention comprising two belts connected to bag portion 3 can be folded into a small volume when not used. Thus, it can be mailed as folded and is very convenient for selling or other purposes.

The bag portion 3 in this embodiment comprises two sheets of cloth superposed and partly sewed together. However, it is not limited to this, but may be, for example, only one sheet of highly stretchable cloth formed so that the hallux can be inserted therein.

FIG. 5 is a schematic plan view showing the usage of the hallux-valgus-remedy brace 1 illustrated in FIG. 1 and includes a partial view of the skeleton around the hallux. With the cushioning member 6 present in contact with the inside of the first metatarsal head, the belt 4 always keeps the first metatarsal pulled toward the second toe (direction of arrow 10) and the belt 4' pulls the dactylopodite bone toward the body center (direction of arrow 11). Thus, the hallux-valgus-remedy brace according to the invention can correct a hallux valgus condition. Because no metallic or plastic material is used in the brace, the brace is, comfortable to wear and can be worn with socks and shoes.

FIG. 6 shows another embodiment of the inserting portion of the hallux-valgus-remedy brace 1 according to the invention. The inserting portion comprises an inserting member 9 sewed to the belt, unlike the above embodiment which has a double structure.

Thus, the hallux-valgus-remedy brace according to the invention has a strong ability to correct a hallux valgus condition, but does not exhibit the rigidness and bulkiness of conventional night braces. The brace can be carried easily because of its light weight, and can be mailed because of its small size.

What is claimed is:

1. A hallux valgus brace adapted to be folded into a small volume, which comprises:
  a bag portion for receiving the hallux of a user's toe, the bag portion being centrally located on the brace;
  foldable first and second belts joined to and extending in opposite directions from the bag portion, each of the first and second belts being formed of an elastic and foldable material, the bag portion being formed of a foldable material similar to the material of which the first and second belts are formed;
  a cushion member removably mounted on the first belt;
  fastening means secured to at least one of said first and second belts for fastening said first and second belts together; and
  a pocket formed on the first belt and situated thereon in proximity to the bag portion, the pocket having opposite open ends, the pocket receiving the second belt therethrough and retaining said cushion in a position adjacent to the metatarsal head of the user's toe, wherein the brace is adapted to be folded in a first storage state and assembled in a second usable state by passing the second belt through the pocket on the first belt and securing the first and second belts to the ankle of the user.

* * * * *